United States Patent [19]

Wriede et al.

[11] Patent Number: 5,123,952

[45] Date of Patent: Jun. 23, 1992

[54] 5-AMINO-6-PYRIDAZONE DERIVATIVES, THEIR PREPARATION AND HERBICIDAL MIXTURES CONTAINING THESE DERIVATIVES

[76] Inventors: Ulrich Wriede, 10 Albert-Einstein-Allee, 6703 Limburgerhof; Bruno Wuerzer, 13 Ruedigerstrasse, 6701 Otterstadt; Norbert Meyer, 22 Dossenheimer Weg, 6802 Ladenburg; Karl-Otto Westphalen, 58 Mausbergweg, 6720 Speyer, all of Fed. Rep. of Germany

[21] Appl. No.: 378,798

[22] Filed: Jul. 12, 1989

[30] Foreign Application Priority Data

Jul. 27, 1988 [DE] Fed. Rep. of Germany ....... 3825468

[51] Int. Cl.[5] .................... A01N 43/48; C07D 237/04
[52] U.S. Cl. ....................... 71/92; 544/239; 544/238
[58] Field of Search ..................... 71/92; 544/238, 239

[56] References Cited

U.S. PATENT DOCUMENTS

| | | | |
|---|---|---|---|
| 3,210,353 | 10/1965 | Reicheneder et al. | 260/250 |
| 3,222,159 | 12/1965 | Reicheneder et al. | 71/2.5 |
| 3,420,819 | 1/1969 | Nakagome et al. | 544/239 |
| 3,652,562 | 3/1972 | Reichender | 71/92 |
| 3,671,525 | 6/1972 | Reicheneder | 344/250 |
| 4,077,797 | 3/1978 | Fischer et al. | 71/92 |

FOREIGN PATENT DOCUMENTS

| | | | |
|---|---|---|---|
| 600532 | 11/1945 | United Kingdom | 544/239 |
| 871674 | 6/1961 | United Kingdom | |

Primary Examiner—C. Warren Ivy
Assistant Examiner—Celia Chang

[57] ABSTRACT

5-Amino-6-pyridazones of the general formulae Ia and Ib

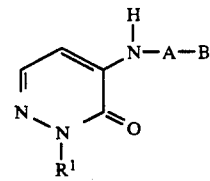

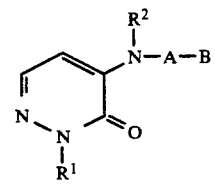

where $R^1$ is $C_1$–$C_4$-alkyl which may carry up to three halogen atoms, $R^2$ is $C_1$–$C_4$-alkyl or $C_3$–$C_6$-alkenyl, where these groups may carry up to two phenyl radicals, or $C_3$–$C_6$-alkynyl, A is —CO— or —SO$_2$—, B is $C_1$–$C_6$-alkyl, $C_2$–$C_6$-alkenyl or $C_2$–$C_6$-alkynyl, where these groups may carry up to three of the following radicals: halogen, $C_1$–$C_4$-alkoxy, $C_1$–$C_4$-alkylthio and/or phenyl; an isocyclic or heterocyclic $C_3$–$C_7$-cycloalkyl group or an isocyclic or heterocyclic $C_3$–$C_7$-cycloalkenyl group, where these groups may be fused with one or two cycloalkyl groups of this type or with one or two benzene nuclei, where the total number of ring members is from 3 to 16 and these cyclic radicals may carry up to three of the following groups: halogen, $C_1$–$C_4$-alkyl, $C_2$–$C_6$-alkenyl, $C_2$–$C_6$-alkynyl and/or phenyl; a mononuclear to trinuclear aromatic or heteroaromatic radical which may carry up to three of the following groups: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkylsulfinyl, $C_1$–$C_4$-alkylsulfonyl, cyano, nitro, carbo-$C_1$–$C_4$-alkoxy, N,N-di-$C_1$–$C_4$-alkylcarbamido and/or halogen.

These compounds are used as herbicidal active ingredients.

11 Claims, No Drawings

5-AMINO-6-PYRIDAZONE DERIVATIVES, THEIR PREPARATION AND HERBICIDAL MIXTURES CONTAINING THESE DERIVATIVES

The present invention relates to 5-amino-6-pyridazones of the formula Ia and/or Ib

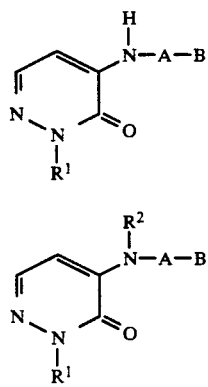

where
- $R^1$ is $C_1-C_4$-alkyl which may carry up to three halogen atoms,
- $R^2$ is $C_1-C_4$-alkyl or $C_3-C_6$-alkenyl, where these groups may carry up to two phenyl radicals, or $C_3-C_6$-alkynyl,
- A is —CO— or —SO$_2$—,
- B is $C_1-C_6$-alkyl, $C_2-C_6$-alkenyl or $C_2-C_6$-alkynyl, where these groups may carry up to three of the following radicals: halogen, $C_1-C_4$-alkoxy, $C_1-C_4$-alkylthio and/or phenyl,
  an isocyclic or heterocyclic $C_3-C_7$-cycloalkyl group or an isocyclic or heterocyclic $C_3-C_7$-cycloalkenyl group, where these groups may be fused with one or two cycloalkyl groups of this type or with one or two benzene nuclei, where the total number of ring members is from 3 to 16 and these cyclic radicals may carry up to three of the following groups: halogen, $C_1-C_4$-alkyl, $C_2-C_6$-alkenyl, $C_2-C_6$-alkynyl and/or phenyl,
  a mononuclear to trinuclear aromatic or heteroaromatic radical which may carry up to three of the following groups: $C_1-C_4$-alkyl, $C_1-C_4$-haloalkyl, $C_1-C_4$-alkoxy, $C_1-C_4$-haloalkoxy, $C_1-C_4$-alkylthio, $C_1-C_4$-alkylsulfinyl, $C_1-C_4$-alkylsulfonyl, cyano, nitro, carbo-$C_1-C_4$-alkoxy, N,N-di-$C_1-C_4$-alkylcarbamido and/or halogen.

The present invention furthermore relates to the preparation of these compounds and their use as herbicides.

DE-B 1 105 232 discloses that N-substituted 4-amino-6-pyridazones have a herbicidal action. Particularly for use in the proximity of crops, for example by the postemergence method, however, it is desirable to have compounds which exhibit higher selectivity at a lower application rate.

We have found that this object is achieved by the 5-amino-6-pyridazone derivatives Ia and Ib defined at the outset.

We have also found that the compounds Ia and Ib have an advantageous herbicidal action, particularly by the postemergence method, and are selective with respect to a number of crops and are accordingly useful as herbicides.

We have furthermore found a process for the preparation of the compounds Ia and Ib.

For the preparation of the novel compounds Ia, a pyridazone II is reacted with hydrazine to give a 5-amino-6-pyridazone III, which is then derivatized with a compound of the formula IV.

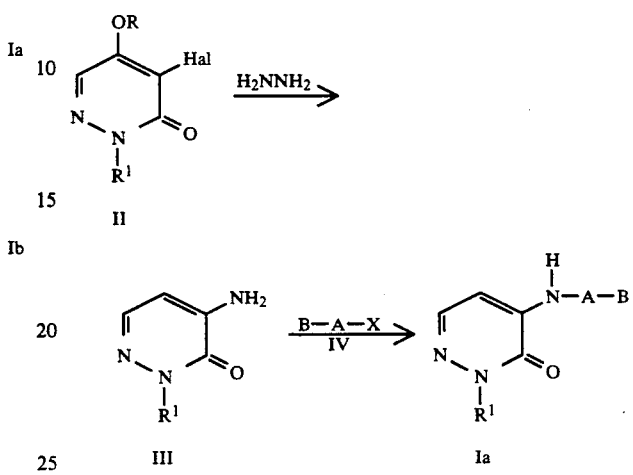

In formula II, R is $C_1-C_4$-alkyl, such as methyl, ethyl, n-propyl, isopropyl and the four isomeric butyl radicals, but in particular methyl or ethyl, and Hal is halogen, such as fluorine, chlorine, bromine or iodine, but in particular chlorine or bromine.

The reduction with hydrazine is preferably carried out in an aqueous medium, with or without the addition of an inert solvent, such as diethyl ether, ethylene glycol dimethyl ether, tetrahydrofuran, methanol, ethanol, isopropanol or dimethyl sulfoxide, at from 20° to 120° C., preferably from 60° to 100° C., continuously or batchwise, under atmospheric or superatmospheric pressure (from 1 to 10 bar).

The subsequent reaction with IV is carried out in a conventional manner (Houben-Weyl, Vol. 8, page 655 et seq. and Vol. E5, page 972 et seq.) preferably under from 0.5 to 10 bar, in particular under atmospheric pressure, continuously or batchwise, at from 0° to 100° C., preferably from 20° to 40° C., in a solvent and in the presence of a base.

In formula IV, X is halogen, e.g. chloride, bromide or iodide, or carboxylate, such as acetate or propionate, but preferably chloride or bromide. As a rule, these radicals can readily be eliminated.

Suitable bases are tertiary amines, such as triethylamine, the picolines, N,N-dimethylaniline or pyridine, or inorganic bases, such as potassium hydroxide, sodium hydroxide, potassium carbonate, sodium bicarbonate, barium hydroxide and sodium acetate. Triethylamine and pyridine are preferred.

Examples of suitable solvents are n-hexane, decalin, toluene, methylene chloride, diethyl ether, tetrahydrofuran, dioxane, dimethylformamide, methanol, ethanol and isopropanol and mixtures of these.

The required pyridazones II are obtained, for example, under the conditions described in German Laid-Open Application DOS 2,526,643, by reacting a dihalo-6-pyridazone of the general formula VI with roughly the stoichiometric amount of an alcoholate of the formula VII, where M is an alkali metal cation, in particular the sodium or potassium ion, and R is alkyl of 1 to 4 carbon atoms, in particular methyl or ethyl, in the presence of an organic solvent, preferably the corresponding alcohol, at from 0° to 100° C., preferably from 10° to 40° C.

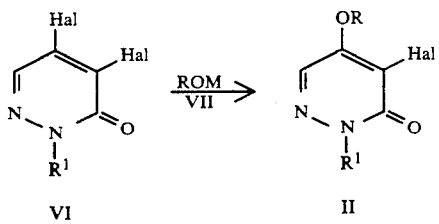

The compounds of the formula Ib are obtained in a conventional manner (Houben-Weyl, Vol. E5, page 998 et seq.) by alkylation, alkenylation or alkynylation of the compounds Ia. For this purpose, the compound Ia is reacted with a reagent of the formula V, where Y is a group which can be readily eliminated, such as halogen, e.g. chloride, bromide or iodide, sulfonate, such as tosylate, mesylate or trifluoromethylsulfonate, or alkylsulfate, such as methylsulfate or ethylsulfate.

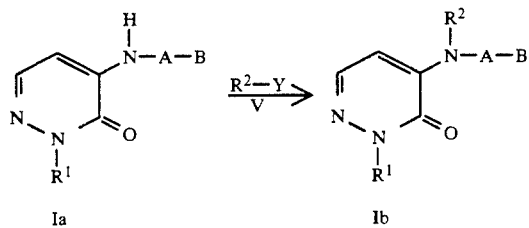

The reaction can be carried out in the presence or absence of a solvent, continuously or batchwise, under atmospheric or superatmospheric pressure (from 1 to 10 bar), at from 20° to 180° C., preferably from 100° to 160° C., in the presence of a strong base.

Suitable bases for this purpose are, for example, sodium hydride, potassium hydride, lithium methylate, sodium methylate, sodium ethylate, potassium tertbutylate, lithium amide, sodium amide, potassium hydroxide and potassium carbonate. Sodium hydride, sodium methylate and potassium tert-butylate are preferred.

Examples of suitable solvents are n-hexane, decalin, toluene, diethyl ether, ethylene glycol dimethyl ether, dioxane, dimethylformamide, dimethyl sulfoxide, acetone, methanol, ethanol and isopropanol. Dimethylformamide is preferred.

To enable the compounds Ia and/or Ib to be used as envisaged as herbicides, the following radicals are suitable:

Suitable alkyl groups $R^1$ are methyl, ethyl, propyl, isopropyl, n-butyl, isobutyl and tert-butyl, preferably methyl or ethyl, and suitable haloalkyl groups $R^1$ are trifluoromethyl, difluoromethyl, fluoromethyl, trichloromethyl, dichloromethyl, chloromethyl, difluorochloromethyl, 1-fluoroethyl, 2-fluoroethyl and 2,2,2-trifluoroethyl, trifluoromethyl and difluoromethyl being preferred.

Suitable alkyl groups $R^2$ are the radicals stated under $R^1$, in particular n-propyl, n-butyl and isobutyl, suitable alkenyl groups $R^2$ are, for example, vinyl, allyl, 2-butenyl, 1-methyl-2-propenyl, 2-methyl-2-propenyl, 2-pentenyl, 1-methyl-2-pentenyl, 2,4-pentadienyl and 1-methyl-2,4-pentadienyl, preferably allyl, and suitable alkynyl groups $R^2$ are, for example, 2-propynyl, 1-methyl-2-propynyl, 2-methyl-2-propynyl and the isomeric pentynyl and hexynyl radicals, 2-propynyl being preferred.

Suitable alkyl groups B are the radicals stated under $R^1$ and n-pentyl, 2-methylbutyl, 3-methylbutyl, 2,2-dimethylpropyl, n-hexyl, 2-methylpentyl, 3-methylpentyl, 4-methylpentyl, 2,2-dimethylbutyl, 3,3-dimethylbutyl, 2,3-dimethylbutyl and 2-ethylbutyl, in particular n-pentyl, 3-methylbutyl, n-hexyl and 4-methylpentyl; suitable alkenyl groups B are vinyl and the radicals stated under $R^2$, 2-methyl-2-propenyl, 2-pentenyl and 2,4-pentadienyl are preferred;

suitable alkynyl groups B are ethynyl and the radicals stated under $R^2$, 3-butynyl, 3-pentynyl and 4-hexynyl are preferred;

suitable cycloalkyl groups B are, for example, cyclopropyl, cyclobutyl, cyclopentyl, cyclohexyl, cycloheptyl and adamantyl as an example of a bridged system, cyclopentyl and cyclohexyl being preferred;

suitable cycloalkenyl groups B are, for example, cyclopropenyl, cyclobutenyl, cyclopentenyl, cyclohexenyl and cycloheptenyl, and norbornenyl as an example of a bridged system, preferably cyclopentenyl, cyclohexenyl and norbornenyl;

suitable heterocyclic aliphatic groups B are, for example, epoxyethyl, oxetanyl, tetrahydrofuranyl, tetrahydropyranyl, thietanyl, tetrahydrothienyl and tetrahydrothiopyranyl, and xanthenyl as an example of a benzofused group, preferably tetrahydrofuranyl, tetrahydropyranyl, tetrahydrothienyl, tetrahydrothiopyranyl and xanthenyl;

suitable heterocyclic alkenyl rings B include dihydrofuranyl, dihydrothienyl and dihydropyranyl, in particular dihydropyranyl and dihydrothienyl;

suitable isoaromatic radicals B are, for example, phenyl, naphthyl, anthracenyl and phenanthrenyl, in particular the phenyl and the naphthyl ring, and suitable heteroaromatic groups B are, for example, pyrrolyl, pyrazolyl, imidazolyl, triazolyl, pyridyl, pyrimidyl, pyrazinyl, pyridazinyl, quinolyl or isoquinolyl, furanyl, thienyl, isoxazolyl, oxazolyl, oxathiazolyl, isothiazolyl, thioxalyl and thiodioxalyl, preferably pyrrolyl, pyrazolyl, imidazolyl, pyridyl, quinolyl, furanyl, thienyl, isoxazolyl, oxazolyl, isothiazoly and thioxazolyl.

Preferred substituents of B are alkyl, such as the radicals stated under $R^1$, in particular methyl, ethyl or isopropyl;

alkenyl, such as vinyl or the radicals stated under $R^2$, preferably vinyl, 2-propenyl or 2-butenyl;

alkynyl, such as ethynyl and the radicals stated under $R^2$, in particular ethynyl or 2-propynyl;

haloalkyl, such as the radicals stated under $R^1$, preferably trifluoromethyl or difluoromethyl;

halogen, such as fluorine, chlorine, bromine or iodine, preferably fluorine or chlorine;

alkoxy, such as methoxy, ethoxy, n-propoxy, isopropoxy or the isomeric butoxy radicals, in particular methoxy or ethoxy, and alkylthio, such as methylthio, ethylthio, n-propylthio, isopropylthio or the isomeric butylthio radicals, in particular methylthio or ethylthio.

The 5-amino-6-pyridazones Ia and/or Ib, or the herbicidal agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives such as methanol, ethanol, propanol, butanol, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, dispersions, wettable powders or water-dispersible granules by adding water. To prepare emulsions, pastes and oil dispersions, the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetate, sorbitol esters, lignin sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations generally contain from 0.1 to 95, and preferably from 0.5 to 90, % by weight of active ingredient. The active ingredients are used in a purity of from 90 to 100, and preferably from 95 to 100, % (according to the NMR spectrum).

The 5-amino-6-pyridazones according to the invention may be formulated for instance as follows:

I. 90 parts by weight of compound no. 1.019 is mixed with 10 parts by weight of N-methyl-alpha-pyrrolidone. A mixture is obtained which is suitable for application in the form of very fine drops.

II. 20 parts by weight of compound no. 1.036 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02 wt % of the active ingredient.

III. 20 parts by weight of compound no. 1.039 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 1.065 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 1.094 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 1.139 is intimately mixed with 97 parts by weight of particulate kaolin. A dust is obtained containing 3% by weight of the active ingredient.

VII. 30 parts by weight of compound no. 1.119 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 2.443 is intimately mixed with 2 parts of the calcium salt of dodecylbenzenesulfonic acid, 8 parts of a fatty alcohol polyglycol ether, 2 parts of the sodium salt of a phenolurea-formaldehyde condensate and 68 parts of a paraffinic mineral oil. A stable oily dispersion is obtained.

The active ingredients may be applied pre- or post-emergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.001 to 5.0, preferably 0.01 to 1.0, kg of active ingredient per hectare.

In view of the number of application methods possible, the compounds according to the invention, or agents containing them, may be used in a further large number of crops for removing unwanted plants. The following crops are given by way of example:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass |
| Daucus carota | carrots |
| Elais guineensis | oil palms |
| Fragaria vesca | strawberries |
| Glycine max | soybeans |
| Gossypium hirsutum (Gossypium arboreum, Gossypium herbaceum, Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |
| Panicum miliaceum | millet |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | sorgo |
| Spinacia oleracea | spinach |
| Theobroma cacao | cacao plants |
| Trifolium pratense | red clover |
| Triticum aestivum | wheat |
| Triticum durum | durum wheat |
| Vaccinium corymbosum | blueberries |
| Vaccinium vitis-idaea | cranberries |
| Vicia faba | tick beans |
| Vigna sinensis (v. unguiculata) | cow peas |
| Vitis vinifera | grapes |
| Zea mays | Indian corn, sweet corn, maize |

To increase the spectrum of action and to achieve synergistic effects, the pyridazones of the formula Ia and/or Ib may be mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, quinolinecarboxylic acids, phenyloxy- and (hetero)aryloxyphenylpropionic acids and salts, esters and amides thereof, etc.

It may also be useful to apply the novel compounds of the formula Ia and/or Ib, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Nonphytotoxic oils and oil concentrates may also be added.

The instructions given in the following synthesis examples were used, after appropriate modification of the starting materials, to obtain further compounds of the formula Ia and/or Ib. The compounds obtained are given with their physical data in the following tables; those compounds without these data may be prepared analogously from the appropriate materials. In view of their structural similarity with the compounds which have been manufactured and investigated, they are expected to have a similar action.

SYNTHESIS EXAMPLES
EXAMPLE 1
5-Acetylamino-1-methyl-6-pyridazone

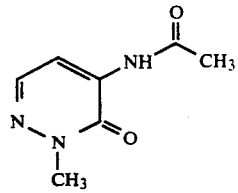

a) At 80° C., 240.8 g (1.38 mol) of 5-chloro-4-methoxy-1-methyl-6-pyridazone was added in portions to 1930 ml of hydrazine hydrate in such a manner that the temperature remained at 80° C. without further heating. After cooling, the precipitate was filtered off, washed and dried. There was obtained 112.8 g (65.3%) of 5-amino-1-methyl-6-pyridazone of melting point 191°–192° C.

The 5-chloro-4-methoxy-1-methyl-6-pyridazone was prepared as follows in accordance with DE-OS 25 26 643:

295 g of 30% strength sodium methylate solution was added to 293 g (1.64 mol) of 4,5-dichloro-1-methyl-6-pyridazone in 690 ml of methanol in such a manner that a temperature of 30° C. was not exceeded. After cooling and stirring for 12 hours at 25° C., the precipitate which had formed was filtered off, washed and dried. There was obtained 241 g (84.3%) of 5-chloro-4-methoxy-1-methyl-6-pyridazone of melting point 189°–191° C.

b) A solution of 2.7 ml of acetyl chloride in 20 ml of dioxane was added dropwise to a solution of 4.0 g (0.032 mol) of 5-amino-1-methyl-6-pyridazone in 100 ml of pyridine. After stirring for 12 hours at 25° C., the solvent was distilled off under reduced pressure, and the residue was taken up with methylene chloride, washed with sodium bicarbonate solution and dried. After the solvent had been stripped off under reduced pressure and the residue stirred with a small amount of diisopropyl ether, there was obtained 3.1 g (58.0%) of 5-acetylamino-1-methyl-6-pyridazone (active ingredient 1.001) of melting point 152°–153° C.

EXAMPLE 2
5-(2-Bromobenzamido)-1-methyl-6-pyridazone

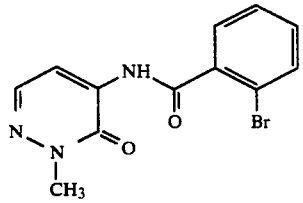

Analogously to Example 1b) 8.0 g (81.2%) 5-(2-bromobenzamido)-1-methyl-6-pyridazone (active ingredient 1.082) of m.p. 190° to 193° C. was obtained from 4.0 g (0.032 mol) of 5-amino-1-methyl-6-pyridazone in 100 ml of pyridine and 7.7 g (0.035 mol) of 2-bromobenzoyl chloride in 20 ml of dioxane.

EXAMPLE 3
5-[N-(2-Bromobenzoyl)-N-methyl]-amino-1-methyl-6-pyridazone

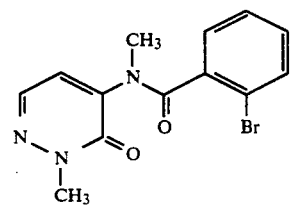

2.9 g of 30% strength sodium methylate solution was added to 4.8 g (0.0156 mol) of 5-(2-bromobenzamido)-1-methyl-6-pyridazone in 50 ml of dimethylformamide. The methanol was then removed completely under reduced pressure and the reaction mixture was stirred for 2.5 hours at 80° C. with 3 g of dimethyl sulfate. Water and 20 ml of concentrated ammonia solution were added and the product was extracted with ethyl acetate. After washing and drying, the organic phase was concentrated. Column chromatography using silica gel (eluant: cyclohexane/ethyl acetate) gave 3.8 g (75.5%) of 5-[N-(2-bromobenzoyl)-N-methyl]-amino-1-methyl-6-pyridazone (active ingredient 2.382) as a viscous oil.

$^1$H-NMR (DMSO-$d_6$): 3.2 (s, 3H), 3.6 (s, 3H), 7.3 (m, 4H), 7.5 (m, 1H), 7.8 (d, I=5 Hz, 1H) ppm.

TABLE 1

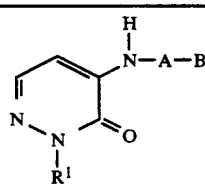

| No. | B | A | $R^1$ | Phys. data mp (°C.) $^1$H-NMR (ppm) |
|---|---|---|---|---|
| 1.001 | methyl | CO | CH$_3$ | 152–153 |
| 1.002 | methyl | SO$_2$ | CH$_3$ | |
| 1.003 | ethyl | CO | CH$_3$ | 115–117 |
| 1.004 | ethyl | SO$_2$ | CH$_3$ | |
| 1.005 | isopropyl | CO | CH$_3$ | |
| 1.006 | tert.-butyl | CO | CH$_3$ | |
| 1.007 | tert.-butylmethyl | CO | CH$_3$ | |
| 1.008 | chloromethyl | CO | CH$_3$ | |

TABLE 1-continued

| No. | B | A | R¹ | Phys. data mp (°C.) ¹H-NMR (ppm) |
|---|---|---|---|---|
| 1.009 | dichloromethyl | CO | $CH_3$ | |
| 1.010 | 2-chloroethyl | CO | $CH_3$ | |
| 1.011 | methoxymethyl | CO | $CH_3$ | |
| 1.012 | ethenyl | CO | $CH_3$ | |
| 1.013 | 1-methylethenyl | CO | $CH_3$ | |
| 1.014 | ethynyl | CO | $CH_3$ | |
| 1.015 | benzyl | CO | $CH_3$ | 154–156 |
| 1.016 | cinnamyl | CO | $CH_3$ | 155–157 |
| 1.017 | cyclopropyl | CO | $CH_3$ | 165–166 |
| 1.018 | 1-methylcyclopropyl | CO | $CH_3$ | |
| 1.019 | 2-methylcyclopropyl | CO | $CH_3$ | 138–140 |
| 1.020 | 1-phenylcyclopropyl | CO | $CH_3$ | |
| 1.021 | 2,2-dichloro-1-methylcyclopropyl | CO | $CH_3$ | |
| 1.022 | cyclopentyl | CO | $CH_3$ | |
| 1.023 | 1-phenylcyclopentyl | CO | $CH_3$ | |
| 1.024 | 9-fluorenyl | CO | $CH_3$ | |
| 1.025 | cyclohexyl | CO | $CH_3$ | 138–139 |
| 1.026 | 1-methylcyclohexyl | CO | $CH_3$ | 95–97 |
| 1.027 | 2-methyl-norborn-2-en-5-yl | CO | $CH_3$ | 104–150 |
| 1.028 | tetrahydropyran-3-yl | CO | $CH_3$ | |
| 1.029 | tetrahydropyran-4-yl | CO | $CH_3$ | |
| 1.030 | 5,6-dihydro-2-methyl-4H-pyran-3-yl | CO | $CH_3$ | 129–130 |
| 1.031 | 5,6-dihydro-2,6,6-trimethyl-4H-pyran-3-yl | CO | $CH_3$ | |
| 1.032 | xanthen-9-yl | CO | $CH_3$ | |
| 1.033 | 5,6-dihydro-3-methyl-4H-thiopyran-2-yl | CO | $CH_3$ | |
| 1.034 | tetrahydrothiopyran-3-yl | CO | $CH_3$ | 156–157 |
| 1.035 | tetrahydrothiopyran-4-yl | CO | $CH_3$ | |
| 1.036 | phenyl | CO | $CH_3$ | 111–112 |
| 1.037 | phenyl | CO | $CH(CH_3)_2$ | |
| 1.038 | phenyl | CO | $C(CH_3)_3$ | |
| 1.039 | phenyl | $SO_2$ | $CH_3$ | 161–163 |
| 1.040 | 2-methylphenyl | CO | $CH_3$ | 144–146 |
| 1.041 | 2-methylphenyl | $SO_2$ | $CH_3$ | |
| 1.042 | 2-methylphenyl | $SO_2$ | $CH_3$ | |
| 1.043 | 4-methylphenyl | CO | $CH_3$ | 151–153 |
| 1.044 | 2,4-dimethylphenyl | CO | $CH_3$ | |
| 1.045 | 2,4-dimethylphenyl | $SO_2$ | $CH_3$ | |
| 1.046 | 2,6-dimethylphenyl | CO | $CH_3$ | |
| 1.047 | 2,6-dimethylphenyl | $SO_2$ | $CH_3$ | |
| 1.048 | 2-trifluoromethylphenyl | CO | $CH_3$ | 185–187 |
| 1.049 | 2-trifluoromethylphenyl | $SO_2$ | $CH_3$ | |
| 1.050 | 2-methoxyphenyl | CO | $CH_3$ | 160–163 |
| 1.051 | 2-methoxyphenyl | $SO_2$ | $CH_3$ | |
| 1.052 | 2,6-dimethoxyphenyl | CO | $CH_3$ | 160–164 |
| 1.053 | 2,6-dimethoxyphenyl | $SO_2$ | $CH_3$ | |
| 1.054 | 2-trifluoromethoxyphenyl | CO | $CH_3$ | |
| 1.055 | 2-methylthiophenyl | CO | $CH_3$ | |
| 1.056 | 2-methylsulfinylphenyl | CO | $CH_3$ | |
| 1.057 | 2-methylsulfonylphenyl | CO | $CH_3$ | |
| 1.058 | 2-fluorophenyl | CO | $CH_3$ | 194–200 |
| 1.059 | 2-fluorophenyl | $SO_2$ | $CH_3$ | |
| 1.060 | 2-fluorophenyl | CO | $CH_2-CF_3$ | |
| 1.061 | 2,3-difluorophenyl | CO | $CH_3$ | |
| 1.062 | 2,4-difluorophenyl | CO | $CH_3$ | 198–200 |
| 1.063 | 2,5-difluorophenyl | CO | $CH_3$ | |
| 1.064 | 2,6-difluorophenyl | CO | $CH_3$ | 198–206 |
| 1.065 | 2-chlorophenyl | CO | $CH_3$ | 176–178 |
| 1.066 | 2-chlorophenyl | $SO_2$ | $CH_3$ | 129–136 |
| 1.067 | 2-chlorophenyl | CO | $CH(CH_3)_2$ | 95–97 |
| 1.068 | 2-chlorophenyl | CO | $C(CH_3)_3$ | 84–86 |
| 1.069 | 2-chlorophenyl | CO | $CH_2CF_3$ | |
| 1.070 | 3-chlorophenyl | CO | $CH_3$ | 151–153 |
| 1.071 | 3-chlorophenyl | $SO_2$ | $CH_3$ | |
| 1.072 | 4-chlorophenyl | CO | $CH_3$ | 231–232 |
| 1.073 | 4-chlorophenyl | $SO_2$ | $CH_3$ | |
| 1.074 | 2,3-dichlorophenyl | CO | $CH_3$ | |
| 1.075 | 2,4-dichlorophenyl | CO | $CH_3$ | 153–154 |
| 1.076 | 2,5-dichlorophenyl | CO | $CH_3$ | 164–166 |
| 1.077 | 2,6-dichlorophenyl | CO | $CH_3$ | |
| 1.078 | 2,6-dichlorophenyl | $SO_2$ | $CH_3$ | |

TABLE 1-continued

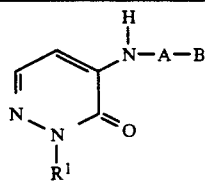

| No. | B | A | R[1] | Phys. data mp (°C.) $^1$H-NMR (ppm) |
|---|---|---|---|---|
| 1.079 | 2,4,6-trichlorophenyl | CO | CH$_3$ | |
| 1.080 | 2-chloro-6-methylphenyl | CO | CH$_3$ | |
| 1.081 | 2-chloro-6-methylphenyl | SO$_2$ | CH$_3$ | |
| 1.082 | 2-bromophenyl | CO | CH$_3$ | 190–193 |
| 1.083 | 2-bromophenyl | SO$_2$ | CH$_3$ | |
| 1.084 | 2-cyanophenyl | CO | CH$_3$ | |
| 1.085 | 2-cyanophenyl | SO$_2$ | CH$_3$ | |
| 1.086 | 2-nitrophenyl | CO | CH$_3$ | 178–186 |
| 1.087 | 2-nitrophenyl | SO$_2$ | CH$_3$ | |
| 1.088 | 2-carbomethoxyphenyl | CO | CH$_3$ | |
| 1.089 | 2-carbomethoxyphenyl | SO$_2$ | CH$_3$ | |
| 1.090 | 2-carbethoxyphenyl | CO | CH$_3$ | |
| 1.091 | 2-carbethoxyphenyl | SO$_2$ | CH$_3$ | |
| 1.092 | 2-(N,N-dimethylcarbamido)phenyl | CO | CH$_3$ | |
| 1.093 | 2-pyridyl | CO | CH$_3$ | |
| 1.094 | 3-pyridyl | CO | CH$_3$ | 136–137 |
| 1.095 | 2-fluoro-3-pyridyl | CO | CH$_3$ | 154–155 |
| 1.096 | 2-chloro-3-pyridyl | CO | CH$_3$ | |
| 1.097 | 4-chloro-3-pyridyl | CO | CH$_3$ | |
| 1.098 | 4-pyridyl | CO | CH$_3$ | |
| 1.099 | 5-pyrimidyl | CO | CH$_3$ | |
| 1.100 | 1-naphthyl | CO | CH$_3$ | |
| 1.101 | 2-naphthyl | CO | CH$_3$ | |
| 1.102 | 2-quinolinyl | CO | CH$_3$ | |
| 1.103 | 3-quinolinyl | CO | CH$_3$ | |
| 1.104 | 2-methyl-4-quinolinyl | CO | CH$_3$ | |
| 1.105 | 3,7-dichloro-8-quinolinyl | CO | CH$_3$ | |
| 1.106 | 7-chloro-3-methyl-8-quinolinyl | CO | CH$_3$ | |
| 1.107 | 7-chloro-3-methyl-8-quinolinyl | CO | CH$_3$ | |
| 1.108 | 2-pyrrolyl | CO | CH$_3$ | |
| 1.109 | 3-pyrrolyl | CO | CH$_3$ | |
| 1.110 | 3-chloro-2-pyrolyl | CO | CH$_3$ | |
| 1.111 | 1-methyl-2-pyrrolyl | CO | CH$_3$ | 137–138 |
| 1.112 | 2-furanyl | CO | CH$_3$ | |
| 1.113 | 3-methyl-2-furanyl | CO | CH$_3$ | |
| 1.114 | 5-bromo-2-furanyl | CO | CH$_3$ | 165–166 |
| 1.115 | 5-methyl-2-furanyl | CO | CH$_3$ | |
| 1.116 | 3-furanyl | CO | CH$_3$ | |
| 1.117 | 2,5-dimethyl-3-furanyl | CO | CH$_3$ | 123–125 |
| 1.118 | 2,4,5-trimethyl-3-furanyl | CO | CH$_3$ | |
| 1.119 | 2-thienyl | CO | CH$_3$ | 162–164 |
| 1.120 | 3-chloro-2-thienyl | CO | CH$_3$ | 224–226 |
| 1.121 | 5-methyl-2-thienyl | CO | CH$_3$ | 147–149 |
| 1.122 | 3-thienyl | CO | CH$_3$ | |
| 1.123 | 4-chloro-3-thienyl | CO | CH$_3$ | 165–167 |
| 1.124 | 1-methyl-5-pyrazolyl | CO | CH$_3$ | |
| 1.125 | 4-pyrazolyl | CO | CH$_3$ | |
| 1.126 | 1-methyl-4-pyrazolyl | CO | CH$_3$ | |
| 1.127 | 3,5-dimethyl-4-pyrazolyl | CO | CH$_3$ | |
| 1.128 | 1-methyl-2-imidazolyl | CO | CH$_3$ | |
| 1.129 | 4-imidazolyl | CO | CH$_3$ | |
| 1.130 | 2-methyl-4-imidazolyl | CO | CH$_3$ | |
| 1.131 | 4-methyl-5-imidazolyl | CO | CH$_3$ | |
| 1.132 | 5-isoxazolyl | CO | CH$_3$ | |
| 1.133 | 4-isoxazolyl | CO | CH$_3$ | |
| 1.134 | 3-isopropyl-5-isoxazolyl | CO | CH$_3$ | 104–105 |
| 1.135 | 3-methyl-4-isoxazolyl | CO | CH$_3$ | |
| 1.136 | 4-isothiazolyl | CO | CH$_3$ | |
| 1.137 | 1-methyl-4-carbethoxy-3-pyrazolyl | CO | CH$_3$ | 194–196 |
| 1.138 | 5-chloro-2-thienyl | CO | CH$_3$ | 158–160 |
| 1.139 | 2-thienyl | SO$_2$ | CH$_3$ | 186–188 |
| 1.140 | 2,5-dichloro-3-thienyl | SO$_2$ | CH$_3$ | 152–154 |
| 1.141 | 2,5-dichloro-3-thienyl | CO | CH$_3$ | 170–171 |
| 1.142 | 3-chloro-2-thienyl | SO$_2$ | CH$_3$ | 185–187 |
| 1.143 | 2-chloro-3-thienyl | CO | CH$_3$ | 185–186 |
| 1.144 | 1-adamantyl | CO | CH$_3$ | 173 |
| 1.145 | cyclobuyl | CO | CH$_3$ | 139–141 |
| 1.146 | 4-methyl-5-oxazolyl | CO | CH$_3$ | |
| 1.147 | 2-methyl-4-oxazolyl | CO | CH$_3$ | |

TABLE 1-continued

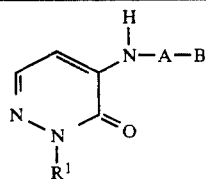

| No. | B | A | R¹ | Phys. data mp (°C.) ¹H-NMR (ppm) |
|---|---|---|---|---|
| 1.148 | 3-isopropyl-4-isoxazolyl | CO | CH₃ | |

TABLE 2

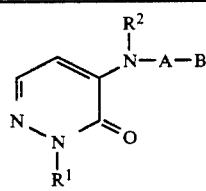

| No. | B | A | R¹ | R² | Phys. data mp (°C.) $^1$H-NMR (ppm) |
|---|---|---|---|---|---|
| 2.001 | methyl | CO | CH₃ | CH₃ | |
| 2.002 | methyl | CO | CH₃ | CH₂CH₂ | |
| 2.003 | methyl | CO | CH₃ | CH(CH₃)₂ | |
| 2.004 | methyl | CO | CH₃ | CH₂CH=CH₂ | |
| 2.005 | methyl | CO | CH₃ | CH₂C≡CH | |
| 2.006 | methyl | CO | CH₃ | CH₂Ph | |
| 2.007 | methyl | SO₂ | CH₃ | CH₃ | |
| 2.008 | methyl | SO₂ | CH₃ | CH₂CH₃ | |
| 2.009 | methyl | SO₂ | CH₃ | CH(CH₃)₂ | |
| 2.010 | methyl | SO₂ | CH₃ | CH₂CH=CH₂ | |
| 2.011 | methyl | SO₂ | CH₃ | CH₂C≡CH | |
| 2.012 | methyl | SO₂ | CH₃ | CH₂Ph | |
| 2.013 | ethyl | CO | CH₃ | CH₃ | |
| 2.014 | ethyl | CO | CH₃ | CH₂CH₃ | |
| 2.015 | ethyl | CO | CH₃ | CH(CH₃)₂ | |
| 2.016 | ethyl | CO | CH₃ | CH₂CH=CH₂ | |
| 2.017 | ethyl | CO | CH₃ | CH₂C≡CH | |
| 2.018 | ethyl | CO | CH₃ | CH₂Ph | |
| 2.019 | ethyl | SO₂ | CH₃ | CH₃ | |
| 2.020 | ethyl | SO₂ | CH₃ | CH₂CH₃ | |
| 2.021 | ethyl | SO₂ | CH₃ | CH(CH₃)₂ | |
| 2.022 | ethyl | SO₂ | CH₃ | CH₂CH=CH₂ | |
| 2.023 | ethyl | SO₂ | CH₃ | CH₂C≡CH | |
| 2.024 | ethyl | SO₂ | CH₃ | CH₂Ph | |
| 2.025 | isopropyl | CO | CH₃ | CH₃ | |
| 2.026 | isopropyl | CO | CH₃ | CH₂CH₃ | |
| 2.027 | isopropyl | CO | CH₃ | CH(CH₃)₂ | |
| 2.028 | isopropyl | CO | CH₃ | CH₂CH=CH₂ | |
| 2.029 | isopropyl | CO | CH₃ | CH₂C≡CH | |
| 2.030 | isopropyl | CO | CH₃ | CH₂Ph | |
| 2.031 | tert.-butyl | CO | CH₃ | CH₃ | |
| 2.032 | tert.-butyl | CO | CH₃ | CH₂CH₃ | |
| 2.033 | tert.-butyl | CO | CH₃ | CH(CH₃)₂ | |
| 2.034 | tert.-butyl | CO | CH₃ | CH₂CH=CH₂ | |
| 2.035 | tert.-butyl | CO | CH₃ | CH₂C≡CH | |
| 2.036 | tert.-butyl | CO | CH₃ | CH₂Ph | |
| 2.037 | tert.-butylmethyl | CO | CH₃ | CH₃ | |
| 2.038 | tert.-butylmethyl | CO | CH₃ | CH₂CH₃ | |
| 2.039 | tert.-butylmethyl | CO | CH₃ | CH(CH₃)₂ | |
| 2.040 | tert.-butylmethyl | CO | CH₃ | CH₂CH=CH₂ | |
| 2.041 | tert.-butylmethyl | CO | CH₃ | CH₂C≡CH | |
| 2.042 | tert.-butylmethyl | CO | CH₃ | CH₂Ph | |
| 2.043 | chloromethyl | CO | CH₃ | CH₃ | |
| 2.044 | chloromethyl | CO | CH₃ | CH₂CH₃ | |
| 2.045 | chloromethyl | CO | CH₃ | CH(CH₃)₂ | |
| 2.046 | chloromethyl | CO | CH₃ | CH₂CH=CH₂ | |
| 2.047 | chloromethyl | CO | CH₃ | CH₂C≡CH | |
| 2.048 | chloromethyl | CO | CH₃ | CH₂Ph | |
| 2.049 | dichloromethyl | CO | CH₃ | CH₃ | |
| 2.050 | dichloromethyl | CO | CH₃ | CH₂CH₃ | |
| 2.051 | dichloromethyl | CO | CH₃ | CH(CH₃)₂ | |
| 2.052 | dichloromethyl | CO | CH₃ | CH₂CH=CH₂ | |
| 2.053 | dichloromethyl | CO | CH₃ | CH₂C≡CH | |

TABLE 2-continued

Structure: pyridazinone with R² on N-A-B substituent, R¹ on ring N

| No. | B | A | R¹ | R² | Phys. data mp (°C.) ¹H-NMR (ppm) |
|---|---|---|---|---|---|
| 2.054 | dichloromethyl | CO | $CH_3$ | $CH_2Ph$ | |
| 2.055 | 2-chloroethyl | CO | $CH_3$ | $CH_3$ | |
| 2.056 | 2-chloroethyl | CO | $CH_3$ | $CH_2CH_3$ | |
| 2.057 | 2-chloroethyl | CO | $CH_3$ | $CH(CH_3)_2$ | |
| 2.058 | 2-chloroethyl | CO | $CH_3$ | $CH_2CH=CH_2$ | |
| 2.059 | 2-chloroethyl | CO | $CH_3$ | $CH_2C\equiv CH$ | |
| 2.060 | 2-chloroethyl | CO | $CH_3$ | $CH_2Ph$ | |
| 2.061 | methoxymethyl | CO | $CH_3$ | $CH_3$ | |
| 2.062 | methoxymethyl | CO | $CH_3$ | $CH_2CH_3$ | |
| 2.063 | methoxymethyl | CO | $CH_3$ | $CH(CH_3)_2$ | |
| 2.064 | methoxymethyl | CO | $CH_3$ | $CH_2CH=CH_2$ | |
| 2.065 | methoxymethyl | CO | $CH_3$ | $CH_2C\equiv CH$ | |
| 2.066 | methoxymethyl | CO | $CH_3$ | $CH_2Ph$ | |
| 2.067 | ethenyl | CO | $CH_3$ | $CH_3$ | |
| 2.068 | 1-methylethenyl | CO | $CH_3$ | $CH_3$ | |
| 2.069 | ethynyl | CO | $CH_3$ | $CH_3$ | |
| 2.070 | benzyl | CO | $CH_3$ | $CH_3$ | |
| 2.071 | cinnamyl | CO | $CH_3$ | $CH_3$ | |
| 2.072 | cyclopropyl | CO | $CH_3$ | $CH_3$ | |
| 2.073 | cyclopropyl | CO | $CH_3$ | $CH_2CH_3$ | |
| 2.074 | cyclopropyl | CO | $CH_3$ | $CH(CH_3)_2$ | |
| 2.075 | cyclopropyl | CO | $CH_3$ | $CH_2CH=CH_2$ | |
| 2.076 | cyclopropyl | CO | $CH_3$ | $CH_2C\equiv CH$ | |
| 2.077 | cyclopropyl | CO | $CH_3$ | $CH_2Ph$ | |
| 2.078 | 1-methylcyclopropyl | CO | $CH_3$ | $CH_3$ | |
| 2.079 | 1-methylcyclopropyl | CO | $CH_3$ | $CH_2CH_3$ | |
| 2.080 | 1-methylcyclopropyl | CO | $CH_3$ | $CH(CH_3)_2$ | |
| 2.081 | 1-methylcyclopropyl | CO | $CH_3$ | $CH_2CH=CH_2$ | |
| 2.082 | 1-methylcyclopropyl | CO | $CH_3$ | $CH_2C\equiv CH$ | |
| 2.083 | 1-methylcyclopropyl | CO | $CH_3$ | $CH_2Ph$ | |
| 2.084 | 2-methylcyclopropyl | CO | $CH_3$ | $CH_3$ | |
| 2.085 | 2-methylcyclopropyl | CO | $CH_3$ | $CH_2CH_3$ | |
| 2.086 | 2-methylcyclopropyl | CO | $CH_3$ | $CH(CH_3)_2$ | |
| 2.087 | 2-methylcyclopropyl | CO | $CH_3$ | $CH_2CH=CH_2$ | |
| 2.088 | 2-methylcyclopropyl | CO | $CH_3$ | $CH_2C\equiv CH$ | |
| 2.089 | 2-methylcyclopropyl | CO | $CH_3$ | $CH_2Ph$ | |
| 2.090 | 1-phenylcyclopropyl | CO | $CH_3$ | $CH_3$ | |
| 2.091 | 1-phenylcyclopropyl | CO | $CH_3$ | $CH_2CH_3$ | |
| 2.092 | 1-phenylcyclopropyl | CO | $CH_3$ | $CH(CH_3)_2$ | |
| 2.093 | 1-phenylcyclopropyl | CO | $CH_3$ | $CH_2CH=CH_2$ | |
| 2.094 | 1-phenylcyclopropyl | CO | $CH_3$ | $CH_2C\equiv CH$ | |
| 2.095 | 1-phenylcyclopropyl | CO | $CH_3$ | $CH_2Ph$ | |
| 2.096 | 2,2-dichloro-1-methyl-cyclopropyl | CO | $CH_3$ | $CH_3$ | |
| 2.097 | 2,2-dichloro-1-methyl-cyclopropyl | CO | $CH_3$ | $CH_2CH_3$ | |
| 2.098 | 2,2-dichloro-1-methyl-cyclopropyl | CO | $CH_3$ | $CH(CH_3)_2$ | |
| 2.099 | 2,2-dichloro-1-methyl-cyclopropyl | CO | $CH_3$ | $CH_2CH=CH_2$ | |
| 2.100 | 2,2-dichloro-1-methyl-cyclopropyl | CO | $CH_3$ | $CH_2C\equiv CH$ | |
| 2.101 | 2,2-dichloro-1-methyl-cyclopropyl | CO | $CH_3$ | $CH_2Ph$ | |
| 2.102 | cyclopentyl | CO | $CH_3$ | $CH_3$ | |
| 2.103 | cyclopentyl | CO | $CH_3$ | $CH_2CH_3$ | |
| 2.104 | cyclopentyl | CO | $CH_3$ | $CH(CH_3)_2$ | |
| 2.105 | cyclopentyl | CO | $CH_3$ | $CH_2CH=CH_2$ | |
| 2.106 | cyclopentyl | CO | $CH_3$ | $CH_2C\equiv CH$ | |
| 2.107 | cyclopentyl | CO | $CH_3$ | $CH_2Ph$ | |
| 2.108 | 1-phenylcyclopentyl | CO | $CH_3$ | $CH_3$ | |
| 2.109 | 1-phenylcyclopentyl | CO | $CH_3$ | $CH_2CH_3$ | |
| 2.110 | 1-phenylcyclopentyl | CO | $CH_3$ | $CH(CH_3)_2$ | |
| 2.111 | 1-phenylcyclopentyl | CO | $CH_3$ | $CH_2CH=CH_2$ | |
| 2.112 | 1-phenylcyclopentyl | CO | $CH_3$ | $CH_2C\equiv CH$ | |
| 2.113 | 1-phenylcyclopentyl | CO | $CH_3$ | $CH_2Ph$ | |
| 2.114 | 9-fluorenyl | CO | $CH_3$ | $CH_3$ | |
| 2.115 | 9-fluorenyl | CO | $CH_3$ | $CH_2CH_3$ | |
| 2.116 | 9-fluorenyl | CO | $CH_3$ | $CH(CH_3)_2$ | |
| 2.117 | 9-fluorenyl | CO | $CH_3$ | $CH_2CH=CH_2$ | |

TABLE 2-continued

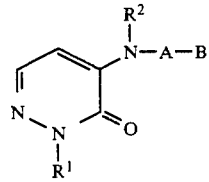

| No. | B | A | R¹ | R² | Phys. data mp (°C.) ¹H-NMR (ppm) |
|---|---|---|---|---|---|
| 2.118 | 9-fluorenyl | CO | $CH_3$ | $CH_2C{\equiv}CH$ | |
| 2.119 | 9-fluorenyl | CO | $CH_3$ | $CH_2Ph$ | |
| 2.120 | cyclohexyl | CO | $CH_3$ | $CH_3$ | |
| 2.121 | cyclohexyl | CO | $CH_3$ | $CH_2CH_3$ | |
| 2.122 | cyclohexyl | CO | $CH_3$ | $CH(CH_3)_2$ | |
| 2.123 | cyclohexyl | CO | $CH_3$ | $CH_2CH{=}CH_2$ | |
| 2.124 | cyclohexyl | CO | $CH_3$ | $CH_2C{\equiv}CH$ | |
| 2.125 | cyclohexyl | CO | $CH_3$ | $CH_2Ph$ | |
| 2.126 | 1-methylcyclohexyl | CO | $CH_3$ | $CH_3$ | |
| 2.127 | 1-methylcyclohexyl | CO | $CH_3$ | $CH_2CH_3$ | |
| 2.128 | 1-methylcyclohexyl | CO | $CH_3$ | $CH(CH_3)_2$ | |
| 2.129 | 1-methylcyclohexyl | CO | $CH_3$ | $CH_2CH{=}CH_2$ | |
| 2.130 | 1-methylcyclohexyl | CO | $CH_3$ | $CH_2C{\equiv}CH$ | |
| 2.131 | 1-methylcyclohexyl | CO | $CH_3$ | $CH_2Ph$ | |
| 2.132 | 5-norbornen-2-yl | CO | $CH_3$ | $CH_3$ | |
| 2.133 | 5-norbornen-2-yl | CO | $CH_3$ | $CH_2CH_3$ | |
| 2.134 | 5-norbornen-2-yl | CO | $CH_3$ | $CH(CH_3)_2$ | |
| 2.135 | 5-norbornen-2-yl | CO | $CH_3$ | $CH_2CH{=}CH_2$ | |
| 2.136 | 5-norbornen-2-yl | CO | $CH_3$ | $CH_2C{\equiv}CH$ | |
| 2.137 | 5-norbornen-2-yl | CO | $CH_3$ | $CH_2Ph$ | |
| 2.138 | tetrahydropyran-3-yl | CO | $CH_3$ | $CH_3$ | |
| 2.139 | tetrahydropyran-3-yl | CO | $CH_3$ | $CH_2CH_3$ | |
| 2.140 | tetrahydropyran-3-yl | CO | $CH_3$ | $CH(CH_3)_2$ | |
| 2.141 | tetrahydropyran-3-yl | CO | $CH_3$ | $CH_2CH{=}CH_2$ | |
| 2.142 | tetrahydropyran-3-yl | CO | $CH_3$ | $CH_2C{\equiv}CH$ | |
| 2.143 | tetrahydropyran-3-yl | CO | $CH_3$ | $CH_2Ph$ | |
| 2.144 | tetrahydropyran-4-yl | CO | $CH_3$ | $CH_3$ | |
| 2.145 | tetrahydropyran-4-yl | CO | $CH_3$ | $CH_2CH_3$ | |
| 2.146 | tetrahydropyran-4-yl | CO | $CH_3$ | $CH(CH_3)_2$ | |
| 2.147 | tetrahydropyran-4-yl | CO | $CH_3$ | $CH_2CH{=}CH_2$ | |
| 2.148 | tetrahydropyran-4-yl | CO | $CH_3$ | $CH_2C{\equiv}CH$ | |
| 2.149 | tetrahydropyran-4-yl | CO | $CH_3$ | $CH_2Ph$ | |
| 2.150 | 5,6-dihydro-2-methyl-4H-pyran-3-yl | CO | $CH_3$ | $CH_3$ | |
| 2.151 | 5,6-dihydro-2-methyl-4H-pyran-3-yl | CO | $CH_3$ | $CH_2CH_3$ | |
| 2.152 | 5,6-dihydro-2-methyl-4H-pyran-3-yl | CO | $CH_3$ | $CH(CH_3)_2$ | |
| 2.153 | 5,6-dihydro-2-methyl-4H-pyran-3-yl | CO | $CH_3$ | $CH_2CH{=}CH_2$ | |
| 2.154 | 5,6-dihydro-2-methyl-4H-pyran-3-yl | CO | $CH_3$ | $CH_2C{\equiv}CH$ | |
| 2.155 | 5,6-dihydro-2-methyl-4H-pyran-3-yl | CO | $CH_3$ | $CH_2Ph$ | |
| 2.156 | 5,6-dihydro-2,6,6-trimethyl-4H-pyran-3-yl | CO | $CH_3$ | $CH_3$ | |
| 2.157 | 5,6-dihydro-2,6,6-trimethyl-4H-pyran-3-yl | CO | $CH_3$ | $CH_2CH_3$ | |
| 2.158 | 5,6-dihydro-2,6,6-trimethyl-4H-pyran-3-yl | CO | $CH_3$ | $CH(CH_3)_2$ | |
| 2.159 | 5,6-dihydro-2,6,6-trimethyl-4H-pyran-3-yl | CO | $CH_3$ | $CH_2CH{=}CH_2$ | |
| 2.160 | 5,6-dihydro-2,6,6-trimethyl-4H-pyran-3-yl | CO | $CH_3$ | $CH_2C{\equiv}CH$ | |
| 2.161 | 5,6-dihydro-2,6,6-trimethyl-4H-pyran-3-yl | CO | $CH_3$ | $CH_2Ph$ | |
| 2.162 | xanthen-9-yl | CO | $CH_3$ | $CH_3$ | |
| 2.163 | xanthen-9-yl | CO | $CH_3$ | $CH_2CH_3$ | |
| 2.164 | xanthen-9-yl | CO | $CH_3$ | $CH(CH_3)_2$ | |
| 2.165 | xanthen-9-yl | CO | $CH_3$ | $CH_2CH{=}CH_2$ | |
| 2.166 | xanthen-9-yl | CO | $CH_3$ | $CH_2C{\equiv}CH$ | |
| 2.167 | xanthen-9-yl | CO | $CH_3$ | $CH_2Ph$ | |
| 2.168 | 5,6-dihydro-3-methyl-4H-thiopyran-2-yl | CO | $CH_3$ | $CH_3$ | |
| 2.169 | 5,6-dihydro-3-methyl-4H-thiopyran-2-yl | CO | $CH_3$ | $CH_2CH_3$ | |
| 2.170 | 5,6-dihydro-3-methyl-4H-thiopyran-2-yl | CO | $CH_3$ | $CH(CH_3)_2$ | |
| 2.171 | 5,6-dihydro-3-methyl-4H-thiopyran-2-yl | CO | $CH_3$ | $CH_2CH{=}CH_2$ | |

TABLE 2-continued

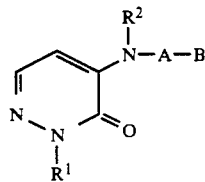

| No. | B | A | R¹ | R² | Phys. data mp (°C.) ¹H-NMR (ppm) |
|---|---|---|---|---|---|
| 2.172 | 5,6-dihydro-3-methyl-4H-thiopyran-2-yl | CO | $CH_3$ | $CH_2C{\equiv}CH$ | |
| 2.173 | 5,6-dihydro-3-methyl-4H-thiopyran-2-yl | CO | $CH_3$ | $CH_2Ph$ | |
| 2.174 | tetrahydrothiopyran-3-yl | CO | $CH_3$ | $CH_3$ | |
| 2.175 | tetrahydrothiopyran-3-yl | CO | $CH_3$ | $CH_2CH_3$ | |
| 2.176 | tetrahydrothiopyran-3-yl | CO | $CH_3$ | $CH(CH_3)_2$ | |
| 2.177 | tetrahydrothiopyran-3-yl | CO | $CH_3$ | $CH_2CH{=}CH_2$ | |
| 2.178 | tetrahydrothiopyran-3-yl | CO | $CH_3$ | $CH_2C{\equiv}CH$ | |
| 2.179 | tetrahydrothiopyran-3-yl | CO | $CH_3$ | $CH_2Ph$ | |
| 2.180 | tetrahydrothiopyran-4-yl | CO | $CH_3$ | $CH_3$ | |
| 2.181 | tetrahydrothiopyran-4-yl | CO | $CH_3$ | $CH_2CH_3$ | |
| 2.182 | tetrahydrothiopyran-4-yl | CO | $CH_3$ | $CH(CH_3)_2$ | |
| 2.183 | tetrahydrothiopyran-4-yl | CO | $CH_3$ | $CH_2CH{=}CH_2$ | |
| 2.184 | tetrahydrothiopyran-4-yl | CO | $CH_3$ | $CH_2C{\equiv}CH$ | |
| 2.185 | tetrahydrothiopyran-4-yl | CO | $CH_3$ | $CH_2Ph$ | |
| 2.186 | phenyl | CO | $CH_3$ | $CH_3$ | |
| 2.187 | phenyl | CO | $CH_3$ | $CH_2CH_3$ | |
| 2.188 | phenyl | CO | $CH_3$ | $CH(CH_3)_2$ | |
| 2.189 | phenyl | CO | $CH_3$ | $CH_2CH{=}CH_2$ | |
| 2.190 | phenyl | CO | $CH_3$ | $CH_2C{\equiv}CH$ | |
| 2.191 | phenyl | CO | $CH_3$ | $CH_2Ph$ | |
| 2.192 | phenyl | CO | $CH(CH_3)_2$ | $CH_3$ | |
| 2.193 | phenyl | CO | $C(CH_3)_3$ | $CH_3$ | |
| 2.194 | phenyl | $SO_2$ | $CH_3$ | $CH_3$ | |
| 2.195 | phenyl | $SO_2$ | $CH_3$ | $CH_2CH_3$ | |
| 2.196 | phenyl | $SO_2$ | $CH_3$ | $CH(CH_3)_2$ | |
| 2.197 | phenyl | $SO_2$ | $CH_3$ | $CH_2CH{=}CH_2$ | |
| 2.198 | phenyl | $SO_2$ | $CH_3$ | $CH_2C{\equiv}CH$ | |
| 2.199 | phenyl | $SO_2$ | $CH_3$ | $CH_2Ph$ | |
| 2.200 | 2-methylphenyl | CO | $CH_3$ | $CH_3$ | |
| 2.201 | 2-methylphenyl | CO | $CH_3$ | $CH_2CH_3$ | |
| 2.202 | 2-methylphenyl | CO | $CH_3$ | $CH(CH_3)_2$ | |
| 2.203 | 2-methylphenyl | CO | $CH_3$ | $CH_2CH{=}CH_2$ | |
| 2.204 | 2-methylphenyl | CO | $CH_3$ | $CH_2C{\equiv}CH$ | |
| 2.205 | 2-methylphenyl | CO | $CH_3$ | $CH_2Ph$ | |
| 2.206 | 2-methylphenyl | $SO_2$ | $CH_3$ | $CH_3$ | |
| 2.207 | 2-methylphenyl | $SO_2$ | $CH_3$ | $CH_2CH_3$ | |
| 2.208 | 2-methylphenyl | $SO_2$ | $CH_3$ | $CH(CH_3)_2$ | |
| 2.209 | 2-methylphenyl | $SO_2$ | $CH_3$ | $CH_2CH{=}CH_2$ | |
| 2.210 | 2-methylphenyl | $SO_2$ | $CH_3$ | $CH_2C{\equiv}CH$ | |
| 2.211 | 2-methylphenyl | $SO_2$ | $CH_3$ | $CH_2Ph$ | |
| 2.212 | 3-methylphenyl | CO | $CH_3$ | $CH_3$ | |
| 2.213 | 4-methylphenyl | CO | $CH_3$ | $CH_3$ | |
| 2.214 | 2,4-dimethylphenyl | CO | $CH_3$ | $CH_3$ | |
| 2.215 | 2,4-dimethylphenyl | CO | $CH_3$ | $CH_2CH_3$ | |
| 2.216 | 2,4-dimethylphenyl | CO | $CH_3$ | $CH(CH_3)_2$ | |
| 2.217 | 2,4-dimethylphenyl | CO | $CH_3$ | $CH_2CH{=}CH_2$ | |
| 2.218 | 2,4-dimethylphenyl | CO | $CH_3$ | $CH_2C{\equiv}CH$ | |
| 2.219 | 2,4-dimethylphenyl | CO | $CH_3$ | $CH_2Ph$ | |
| 2.220 | 2,4-dimethylphenyl | $SO_2$ | $CH_3$ | $CH_3$ | |
| 2.221 | 2,4-dimethylphenyl | $SO_2$ | $CH_3$ | $CH_2CH_3$ | |
| 2.222 | 2,4-dimethylphenyl | $SO_2$ | $CH_3$ | $CH(CH_3)_2$ | |
| 2.223 | 2,4-dimethylphenyl | $SO_2$ | $CH_3$ | $CH_2CH{=}CH_2$ | |
| 2.224 | 2,4-dimethylphenyl | $SO_2$ | $CH_3$ | $CH_2C{\equiv}CH$ | |
| 2.225 | 2,4-dimethylphenyl | $SO_2$ | $CH_3$ | $CH_2Ph$ | |
| 2.226 | 2,6-dimethylphenyl | CO | $CH_3$ | $CH_3$ | |
| 2.227 | 2,6-dimethylphenyl | CO | $CH_3$ | $CH_2CH_3$ | |

TABLE 2-continued

Structure:

$$\text{pyridazinone with } R^2\text{-N-A-B substituent at position 4, } R^1 \text{ on ring N}$$

| No. | B | A | R$^1$ | R$^2$ | Phys. data mp (°C.) $^1$H-NMR (ppm) |
|---|---|---|---|---|---|
| 2.228 | 2,6-dimethylphenyl | CO | CH$_3$ | CH(CH$_3$)$_2$ | |
| 2.229 | 2,6-dimethylphenyl | CO | CH$_3$ | CH$_2$CH=CH$_2$ | |
| 2.230 | 2,6-dimethylphenyl | CO | CH$_3$ | CH$_2$C≡CH | |
| 2.231 | 2,6-dimethylphenyl | CO | CH$_3$ | CH$_2$Ph | |
| 2.232 | 2,6-dimethylphenyl | SO$_2$ | CH$_3$ | CH$_3$ | |
| 2.233 | 2,6-dimethylphenyl | SO$_2$ | CH$_3$ | CH$_2$CH$_3$ | |
| 2.234 | 2,6-dimethylphenyl | SO$_2$ | CH$_3$ | CH(CH$_3$)$_2$ | |
| 2.235 | 2,6-dimethylphenyl | SO$_2$ | CH$_3$ | CH$_2$CH=CH$_2$ | |
| 2.236 | 2,6-dimethylphenyl | SO$_2$ | CH$_3$ | CH$_2$C≡CH | |
| 2.237 | 2,6-dimethylphenyl | SO$_2$ | CH$_3$ | CH$_2$Ph | |
| 2.238 | 2-trifluoromethylphenyl | CO | CH$_3$ | CH$_3$ | |
| 2.239 | 2-trifluoromethylphenyl | CO | CH$_3$ | CH$_2$CH$_3$ | |
| 2.240 | 2-trifluoromethylphenyl | CO | CH$_3$ | CH(CH$_3$)$_2$ | |
| 2.241 | 2-trifluoromethylphenyl | CO | CH$_3$ | CH$_2$CH=CH$_2$ | |
| 2.242 | 2-trifluoromethylphenyl | CO | CH$_3$ | CH$_2$C≡CH | |
| 2.243 | 2-trifluoromethylphenyl | CO | CH$_3$ | CH$_2$Ph | |
| 2.244 | 2-trifluoromethylphenyl | SO$_2$ | CH$_3$ | CH$_3$ | |
| 2.245 | 2-methoxyphenyl | CO | CH$_3$ | CH$_3$ | |
| 2.246 | 2-methoxyphenyl | CO | CH$_3$ | CH$_2$CH$_3$ | |
| 2.247 | 2-methoxyphenyl | CO | CH$_3$ | CH(CH$_3$)$_2$ | |
| 2.248 | 2-methoxyphenyl | CO | CH$_3$ | CH$_2$CH=CH$_2$ | |
| 2.249 | 2-methoxyphenyl | CO | CH$_3$ | CH$_2$C≡CH | |
| 2.250 | 2-methoxyphenyl | CO | CH$_3$ | CH$_2$Ph | |
| 2.251 | 2-methoxyphenyl | SO$_2$ | CH$_3$ | CH$_3$ | |
| 2.252 | 2,6-dimethoxyphenyl | CO | CH$_3$ | CH$_3$ | |
| 2.253 | 2,6-dimethoxyphenyl | CO | CH$_3$ | CH$_2$CH$_3$ | |
| 2.254 | 2,6-dimethoxyphenyl | CO | CH$_3$ | CH(CH$_3$)$_2$ | |
| 2.255 | 2,6-dimethoxyphenyl | CO | CH$_3$ | CH$_2$CH=CH$_2$ | |
| 2.256 | 2,6-dimethoxyphenyl | CO | CH$_3$ | CH$_2$C≡CH | |
| 2.257 | 2,6-dimethoxyphenyl | CO | CH$_3$ | CH$_2$Ph | |
| 2.258 | 2,6-dimethoxyphenyl | SO$_2$ | CH$_3$ | CH$_3$ | |
| 2.259 | 2-trifluoromethoxyphenyl | CO | CH$_3$ | CH$_3$ | |
| 2.260 | 2-trifluoromethoxyphenyl | CO | CH$_3$ | CH$_2$CH$_3$ | |
| 2.261 | 2-trifluoromethoxyphenyl | CO | CH$_3$ | CH(CH$_3$)$_2$ | |
| 2.262 | 2-trifluoromethoxyphenyl | CO | CH$_3$ | CH$_2$CH=CH$_2$ | |
| 2.263 | 2-trifluoromethoxyphenyl | CO | CH$_3$ | CH$_2$C≡CH | |
| 2.264 | 2-trifluoromethoxyphenyl | CO | CH$_3$ | CH$_2$Ph | |
| 2.265 | 2-methylthiophenyl | CO | CH$_3$ | CH$_3$ | |
| 2.266 | 2-methylsulfinylphenyl | CO | CH$_3$ | CH$_3$ | |
| 2.267 | 2-methylsulfonylphenyl | CO | CH$_3$ | CH$_3$ | |
| 2.268 | 2-fluorophenyl | CO | CH$_3$ | CH$_3$ | |
| 2.269 | 2-fluorophenyl | CO | CH$_3$ | CH$_2$CH$_3$ | |
| 2.270 | 2-fluorophenyl | CO | CH$_3$ | CH(CH$_3$)$_2$ | |
| 2.271 | 2-fluorophenyl | CO | CH$_3$ | CH$_2$CH=CH$_2$ | 75–77 |
| 2.272 | 2-fluorophenyl | CO | CH$_3$ | CH$_2$C≡CH | |
| 2.273 | 2-fluorophenyl | CO | CH$_3$ | CH$_2$Ph | 98–100 |
| 2.274 | 2-fluorophenyl | SO$_2$ | CH$_3$ | CH$_3$ | |
| 2.275 | 2-fluorophenyl | SO$_2$ | CH$_3$ | CH$_2$CH$_3$ | |
| 2.276 | 2-fluorophenyl | SO$_2$ | CH$_3$ | CH(CH$_3$)$_2$ | |
| 2.277 | 2-fluorophenyl | SO$_2$ | CH$_3$ | CH$_2$CH=CH$_2$ | |
| 2.278 | 2-fluorophenyl | SO$_2$ | CH$_3$ | CH$_2$C≡CH | |
| 2.279 | 2-fluorophenyl | SO$_2$ | CH$_3$ | CH$_2$Ph | |
| 2.280 | 2-fluorophenyl | CO | CH$_2$CF$_3$ | CH$_3$ | |
| 2.281 | 2-fluorophenyl | CO | CH$_2$CF$_3$ | CH$_2$CH$_3$ | |
| 2.282 | 2-fluorophenyl | CO | CH$_2$CF$_3$ | CH(CH$_3$)$_2$ | |
| 2.283 | 2-fluorophenyl | CO | CH$_2$CF$_3$ | CH$_2$CH=CH$_2$ | |
| 2.284 | 2-fluorophenyl | CO | CH$_2$CF$_3$ | CH$_2$C≡CH | |
| 2.285 | 2-fluorophenyl | CO | CH$_2$CF$_3$ | CH$_2$Ph | |
| 2.286 | 2,3-difluorophenyl | CO | CH$_3$ | CH$_3$ | |
| 2.287 | 2,3-difluorophenyl | CO | CH$_3$ | CH$_2$CH$_3$ | |
| 2.288 | 2,3-difluorophenyl | CO | CH$_3$ | CH(CH$_3$)$_2$ | |
| 2.289 | 2,3-difluorophenyl | CO | CH$_3$ | CH$_2$CH=CH$_2$ | |
| 2.290 | 2,3-difluorophenyl | CO | CH$_3$ | CH$_2$C≡CH | |
| 2.291 | 2,3-difluorophenyl | CO | CH$_3$ | CH$_2$Ph | |
| 2.292 | 2,4-difluorophenyl | CO | CH$_3$ | CH$_3$ | |
| 2.293 | 2,4-difluorophenyl | CO | CH$_3$ | CH$_2$CH$_3$ | |
| 2.294 | 2,4-difluorophenyl | CO | CH$_3$ | CH(CH$_3$)$_2$ | |
| 2.295 | 2,4-difluorophenyl | CO | CH$_3$ | CH$_2$CH=CH$_2$ | |
| 2.296 | 2,4-difluorophenyl | CO | CH$_3$ | CH$_2$C≡CH | |
| 2.297 | 2,4-difluorophenyl | CO | CH$_3$ | CH$_2$Ph | |

TABLE 2-continued

Structure: pyridazinone with N-A-B and R² substituent, R¹ on ring N, =O.

| No. | B | A | R¹ | R² | Phys. data mp (°C.) ¹H-NMR (ppm) |
|---|---|---|---|---|---|
| 2.298 | 2,5-difluorophenyl | CO | $CH_3$ | $CH_3$ | |
| 2.299 | 2,5-difluorophenyl | CO | $CH_3$ | $CH_2CH_3$ | |
| 2.300 | 2,5-difluorophenyl | CO | $CH_3$ | $CH(CH_3)_2$ | |
| 2.301 | 2,5-difluorophenyl | CO | $CH_3$ | $CH_2CH=CH_2$ | |
| 2.302 | 2,5-difluorophenyl | CO | $CH_3$ | $CH_2C\equiv CH$ | |
| 2.303 | 2,5-difluorophenyl | CO | $CH_3$ | $CH_2Ph$ | |
| 2.304 | 2,6-difluorophenyl | CO | $CH_3$ | $CH_3$ | |
| 2.305 | 2,6-difluorophenyl | CO | $CH_3$ | $CH_2CH_3$ | |
| 2.306 | 2,6-difluorophenyl | CO | $CH_3$ | $CH(CH_3)_2$ | |
| 2.307 | 2,6-difluorophenyl | CO | $CH_3$ | $CH_2CH=CH_2$ | |
| 2.308 | 2,6-difluorophenyl | CO | $CH_3$ | $CH_2C\equiv CH$ | |
| 2.309 | 2,6-difluorophenyl | CO | $CH_3$ | $CH_2Ph$ | |
| 2.310 | 2-chlorophenyl | CO | $CH_3$ | $CH_3$ | |
| 2.311 | 2-chlorophenyl | CO | $CH_3$ | $CH_2CH_3$ | |
| 2.312 | 2-chlorophenyl | CO | $CH_3$ | $CH(CH_3)_2$ | |
| 2.313 | 2-chlorophenyl | CO | $CH_3$ | $CH_2CH=CH_2$ | |
| 2.314 | 2-chlorophenyl | CO | $CH_3$ | $CH_2C\equiv CH$ | |
| 2.315 | 2-chlorophenyl | CO | $CH_3$ | $CH_2Ph$ | |
| 2.316 | 2-chlorophenyl | $SO_2$ | $CH_3$ | $CH_3$ | |
| 2.317 | 2-chlorophenyl | $SO_2$ | $CH_3$ | $CH_2CH_3$ | |
| 2.318 | 2-chlorophenyl | $SO_2$ | $CH_3$ | $CH(CH_3)_2$ | |
| 2.319 | 2-chlorophenyl | $SO_2$ | $CH_3$ | $CH_2CH=CH_2$ | |
| 2.320 | 2-chlorophenyl | $SO_2$ | $CH_3$ | $CH_2C\equiv CH$ | |
| 2.321 | 2-chlorophenyl | $SO_2$ | $CH_3$ | $CH_2Ph$ | |
| 2.322 | 2-chlorophenyl | CO | $CH(CH_3)_2$ | $CH_3$ | |
| 2.323 | 2-chlorophenyl | CO | $C(CH_3)_3$ | $CH_3$ | |
| 2.324 | 2-chlorophenyl | CO | $CH_2CF_3$ | $CH_3$ | |
| 2.325 | 2-chlorophenyl | CO | $CH_2CF_3$ | $CH_2CH_3$ | |
| 2.326 | 2-chlorophenyl | CO | $CH_2CF_3$ | $CH(CH_3)_2$ | |
| 2.327 | 2-chlorophenyl | CO | $CH_2CF_3$ | $CH_2CH=CH_2$ | |
| 2.328 | 2-chlorophenyl | CO | $CH_2CF_3$ | $CH_2C\equiv CH$ | |
| 2.329 | 2-chlorophenyl | CO | $CH_2CF_3$ | $CH_2Ph$ | |
| 2.330 | 3-chlorophenyl | CO | $CH_3$ | $CH_3$ | |
| 2.331 | 3-chlorophenyl | $SO_2$ | $CH_3$ | $CH_3$ | |
| 2.332 | 4-chlorophenyl | CO | $CH_3$ | $CH_3$ | |
| 2.333 | 4-chlorophenyl | $SO_2$ | $CH_3$ | $CH_3$ | |
| 2.334 | 2,3-dichlorophenyl | CO | $CH_3$ | $CH_3$ | |
| 2.335 | 2,3-dichlorophenyl | CO | $CH_3$ | $CH_2CH_3$ | |
| 2.336 | 2,3-dichlorophenyl | CO | $CH_3$ | $CH(CH_3)_2$ | |
| 2.337 | 2,3-dichlorophenyl | CO | $CH_3$ | $CH_2CH=CH_2$ | |
| 2.338 | 2,3-dichlorophenyl | CO | $CH_3$ | $CH_2C\equiv CH$ | |
| 2.339 | 2,3-dichlorophenyl | CO | $CH_3$ | $CH_2Ph$ | |
| 2.340 | 2,4-dichlorophenyl | CO | $CH_3$ | $CH_3$ | |
| 2.341 | 2,4-dichlorophenyl | CO | $CH_3$ | $CH_2CH_3$ | |
| 2.342 | 2,4-dichlorophenyl | CO | $CH_3$ | $CH(CH_3)_2$ | |
| 2.343 | 2,4-dichlorophenyl | CO | $CH_3$ | $CH_2CH=CH_2$ | |
| 2.344 | 2,4-dichlorophenyl | CO | $CH_3$ | $CH_2C\equiv CH$ | |
| 2.345 | 2,4-dichlorophenyl | CO | $CH_3$ | $CH_2Ph$ | |
| 2.346 | 2,5-dichlorophenyl | CO | $CH_3$ | $CH_3$ | |
| 2.347 | 2,5-dichlorophenyl | CO | $CH_3$ | $CH_2CH_3$ | |
| 2.348 | 2,5-dichlorophenyl | CO | $CH_3$ | $CH(CH_3)_2$ | |
| 2.349 | 2,5-dichlorophenyl | CO | $CH_3$ | $CH_2CH=CH_2$ | |
| 2.350 | 2,5-dichlorophenyl | CO | $CH_3$ | $CH_2C\equiv CH$ | |
| 2.351 | 2,5-dichlorophenyl | CO | $CH_3$ | $CH_2Ph$ | |
| 2.352 | 2,6-dichlorophenyl | CO | $CH_3$ | $CH_3$ | |
| 2.353 | 2,6-dichlorophenyl | CO | $CH_3$ | $CH_2CH_3$ | |
| 2.354 | 2,6-dichlorophenyl | CO | $CH_3$ | $CH(CH_3)_2$ | |
| 2.355 | 2,6-dichlorophenyl | CO | $CH_3$ | $CH_2CH=CH_2$ | |
| 2.356 | 2,6-dichlorophenyl | CO | $CH_3$ | $CH_2C\equiv CH$ | |
| 2.357 | 2,6-dichlorophenyl | CO | $CH_3$ | $CH_2Ph$ | |
| 2.358 | 2,6-dichlorophenyl | $SO_2$ | $CH_3$ | $CH_3$ | |
| 2.359 | 2,6-dichlorophenyl | $SO_2$ | $CH_3$ | $CH_2CH_3$ | |
| 2.360 | 2,6-dichlorophenyl | $SO_2$ | $CH_3$ | $CH(CH_3)_2$ | |
| 2.361 | 2,6-dichlorophenyl | $SO_2$ | $CH_3$ | $CH_2CH=CH_2$ | |
| 2.362 | 2,6-dichlorophenyl | $SO_2$ | $CH_3$ | $CH_2C\equiv CH$ | |
| 2.363 | 2,6-dichlorophenyl | $SO_2$ | $CH_3$ | $CH_2Ph$ | |
| 2.364 | 2,4,6-trichlorophenyl | CO | $CH_3$ | $CH_3$ | |
| 2.365 | 2,4,6-trichlorophenyl | CO | $CH_3$ | $CH_2CH_3$ | |
| 2.366 | 2,4,6-trichlorophenyl | CO | $CH_3$ | $CH(CH_3)_2$ | |
| 2.367 | 2,4,6-trichlorophenyl | CO | $CH_3$ | $CH_2CH=CH_2$ | |

TABLE 2-continued $$\text{Structure with pyridazinone ring bearing } R^1 \text{ on N, =O, and } N(R^2)-A-B \text{ substituent}$$

| No. | B | A | R¹ | R² | Phys. data mp (°C.) ¹H-NMR (ppm) |
|---|---|---|---|---|---|
| 2.368 | 2,4,6-trichlorophenyl | CO | CH₃ | CH₂C≡CH | |
| 2.369 | 2,4,6-trichlorophenyl | CO | CH₃ | CH₂Ph | |
| 2.370 | 2-chloro-6-methylphenyl | CO | CH₃ | CH₃ | |
| 2.371 | 2-chloro-6-methylphenyl | CO | CH₃ | CH₂CH₃ | |
| 2.372 | 2-chloro-6-methylphenyl | CO | CH₃ | CH(CH₃)₂ | |
| 2.373 | 2-chloro-6-methylphenyl | CO | CH₃ | CH₂CH=CH₂ | |
| 2.374 | 2-chloro-6-methylphenyl | CO | CH₃ | CH₂C≡CH | |
| 2.375 | 2-chloro-6-methylphenyl | CO | CH₃ | CH₂Ph | |
| 2.376 | 2-chloro-6-methylphenyl | SO₂ | CH₃ | CH₃ | |
| 2.377 | 2-chloro-6-methylphenyl | SO₂ | CH₃ | CH₂CH₃ | |
| 2.378 | 2-chloro-6-methylphenyl | SO₂ | CH₃ | CH(CH₃)₂ | |
| 2.379 | 2-chloro-6-methylphenyl | SO₂ | CH₃ | CH₂CH=CH₂ | |
| 2.380 | 2-chloro-6-methylphenyl | SO₂ | CH₃ | CH₂C≡CH | |
| 2.381 | 2-chloro-6-methylphenyl | SO₂ | CH₃ | CH₂Ph | |
| 2.382 | 2-bromophenyl | CO | CH₃ | CH₃ | 3.23(s)3H;3.63(s)3H; 7.32(m)4H;7.58(m)1H; 7,82(d)1H;J=5Hz |
| 2.383 | 2-bromophenyl | CO | CH₃ | CH₂CH₃ | |
| 2.384 | 2-bromophenyl | CO | CH₃ | CH(CH₃)₂ | |
| 2.385 | 2-bromophenyl | CO | CH₃ | CH₂CH=CH₂ | |
| 2.386 | 2-bromophenyl | CO | CH₃ | CH₂C≡CH | |
| 2.387 | 2-bromophenyl | CO | CH₃ | CH₂Ph | |
| 2.388 | 2-cyanophenyl | CO | CH₃ | CH₃ | |
| 2.389 | 2-cyanophenyl | CO | CH₃ | CH₂CH₃ | |
| 2.390 | 2-cyanophenyl | CO | CH₃ | CH(CH₃)₂ | |
| 2.391 | 2-cyanophenyl | CO | CH₃ | CH₂CH=CH₂ | |
| 2.392 | 2-cyanophenyl | CO | CH₃ | CH₂C≡CH | |
| 2.393 | 2-cyanophenyl | CO | CH₃ | CH₂Ph | |
| 2.394 | 2-cyanophenyl | SO₂ | CH₃ | CH₃ | |
| 2.395 | 2-nitrophenyl | CO | CH₃ | CH₃ | |
| 2.396 | 2-nitrophenyl | CO | CH₃ | CH₂CH₃ | |
| 2.397 | 2-nitrophenyl | SO₂ | CH₃ | CH₂CH₃ | |
| 2.398 | 2-nitrophenyl | CO | CH₃ | CH(CH₃)₂ | |
| 2.399 | 2-nitrophenyl | CO | CH₃ | CH₂CH=CH₂ | |
| 2.400 | 2-nitrophenyl | CO | CH₃ | CH₂C≡CH | |
| 2.401 | 2-nitrophenyl | CO | CH₃ | CH₂Ph | |
| 2.402 | 2-nitrophenyl | SO₂ | CH₃ | CH₃ | |
| 2.403 | 2-carbomethoxyphenyl | CO | CH₃ | CH₃ | |
| 2.404 | 2-carbomethoxyphenyl | CO | CH₃ | CH₂CH₃ | |
| 2.405 | 2-carbomethoxyphenyl | CO | CH₃ | CH(CH₃)₂ | |
| 2.406 | 2-carbomethoxyphenyl | CO | CH₃ | CH₂CH=CH₂ | |
| 2.407 | 2-carbomethoxyphenyl | CO | CH₃ | CH₂C≡CH | |
| 2.408 | 2-carbomethoxyphenyl | CO | CH₃ | CH₂Ph | |
| 2.409 | 2-carbomethoxyphenyl | SO₂ | CH₃ | CH₃ | |
| 2.410 | 2-carbethoxyphenyl | CO | CH₃ | CH₃ | |
| 2.411 | 2-carbethoxyphenyl | SO₂ | CH₃ | CH₃ | |
| 2.412 | 2-(N,N-dimethylcarbamido)phenyl | CO | CH₃ | CH₃ | |
| 2.413 | 2-pyridyl | CO | CH₃ | CH₃ | |
| 2.414 | 3-pyridyl | CO | CH₃ | CH₃ | |
| 2.415 | 2-fluoro-3-pyridyl | CO | CH₃ | CH₃ | |
| 2.416 | 2-chloro-3-pyridyl | CO | CH₃ | CH₃ | |
| 2.417 | 4-chloro-3-pyridyl | CO | CH₃ | CH₃ | |
| 2.418 | 4-pyridyl | CO | CH₃ | CH₃ | |
| 2.419 | 5-pyrimidyl | CO | CH₃ | CH₃ | |
| 2.420 | 1-naphthyl | CO | CH₃ | CH₃ | |
| 2.421 | 2-naphthyl | CO | CH₃ | CH₃ | |
| 2.422 | 2-quinolinyl | CO | CH₃ | CH₃ | |
| 2.423 | 3-quinolinyl | CO | CH₃ | CH₃ | |
| 2.424 | 2-methyl-4-quinolinyl- | CO | CH₃ | CH₃ | |
| 2.425 | 3,7-dichloro-8-quinolinyl | CO | CH₃ | CH₃ | |
| 2.426 | 1-methyl-2-pyrrolyl | CO | CH₃ | CH₃ | |
| 2.427 | 2-furanyl | CO | CH₃ | CH₃ | |
| 2.428 | 3-methyl-2-furanyl | CO | CH₃ | CH₃ | |
| 2.429 | 5-bromo-2-furanyl | CO | CH₃ | CH₃ | |
| 2.430 | 5-methyl-2-furanyl | CO | CH₃ | CH₃ | |
| 2.431 | 3-furanyl | CO | CH₃ | CH₃ | |
| 2.432 | 2,5-dimethyl-3-furanyl | CO | CH₃ | CH₃ | |
| 2.433 | 2,4,5-trimethyl-3- | CO | CH₃ | CH₃ | |

TABLE 2-continued

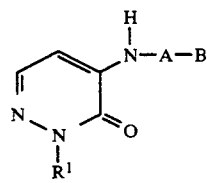

| No. | B | A | R¹ | R² | Phys. data mp (°C.) ¹H-NMR (ppm) |
|---|---|---|---|---|---|
| | furanyl | | | | |
| 2.434 | 2-thienyl | CO | $CH_3$ | $CH_3$ | |
| 2.435 | 2-thienyl | CO | $CH_3$ | $CH_2CH_3$ | |
| 2.436 | 2-thienyl | CO | $CH_3$ | $CH(CH_3)_2$ | |
| 2.437 | 2-thienyl | CO | $CH_3$ | $CH_2CH=CH_2$ | |
| 2.438 | 2-thienyl | CO | $CH_3$ | $CH_2C\equiv CH$ | |
| 2.439 | 2-thienyl | CO | $CH_3$ | $CH_2Ph$ | |
| 2.440 | 3-chloro-2-thienyl | CO | $CH_3$ | $CH_3$ | 3.24(s)3H;3.60(s) 3H;7.32;7.56;7.64; 7.87;each(d) 1H; I=4Hz |
| 2.441 | 5-methyl-2-thienyl | CO | $CH_3$ | $CH_3$ | |
| 2.442 | 3-thienyl | CO | $CH_3$ | $CH_3$ | |
| 2.443 | 4-chloro-3-thienyl | CO | $CH_3$ | $CH_3$ | 168-171 |
| 2.444 | 1-methyl-5-pyrazolyl | CO | $CH_3$ | $CH_3$ | |
| 2.445 | 1-methyl-4-pyrazolyl | CO | $CH_3$ | $CH_3$ | |
| 2.446 | 1-methyl-2-imidazolyl | CO | $CH_3$ | $CH_3$ | |
| 2.447 | 5-isoxazolyl | CO | $CH_3$ | $CH_3$ | |
| 2.448 | 4-isoxazolyl | CO | $CH_3$ | $CH_3$ | |
| 2.449 | 3-isopropyl-5-isoxazolyl | CO | $CH_3$ | $CH_3$ | |
| 2.450 | 3-methyl-4-isoxazolyl | CO | $CH_3$ | $CH_3$ | |
| 2.451 | 4-isothiazolyl | CO | $CH_3$ | $CH_3$ | |

USE EXAMPLES

The action of the 5-amino-6-pyridazone derivatives I on the growth of test plants is illustrated in the following greenhouse experiments.

The vessels employed were plastic flowerpots having a volume of 300 cm³ and filled with a sandy loam containing about 3.0% humus. The seeds of the test plants were sown separately, according to species.

For postemergence treatment, either plants which had been sown in the pots and grown there were selected, or they were cultivated separately as seedlings and transplanted to the pots a few days before being treated. The plants were grown, depending on growth form, to a height of 3 to 15 cm before being treated with the active ingredients, which were suspended or emulsified in water as vehicle, and sprayed through finely distributing nozzles. The application rate for postemergence treatment was 0.25 kg/ha.

The pots were set up in the greenhouse, species from warmer climates in warmer areas (20° to 35° C.) and species from moderate climates at 10° to 20° C. The experiments were run for from 2 to 4 weeks. During this time the plants were tended and their reactions to the various treatments assessed. The assessment scale was 0 to 100, 100 denoting nonemergence or complete destruction of at least the visible plant parts, and 0 denoting no damage or normal growth.

The plants used in the greenhouse experiments were *Chenopodium album*, *Stellaria media* and *Triticum aestivum*.

The compounds 1.036, 1.039 and 1.065, applied postemergence at a rate of 0.250 kg/ha, combated unwanted plants extremely well and were well tolerated by wheat.

The compound 1.123, applied postemergence at a rate of 0.125 kg/ha, combated unwanted plants very well and was well tolerated by wheat.

We claim:
1. A 5-amino-6-pyridazone compound of the formula Ia where R¹ is $C_1$-$C_4$-alkyl which may carry up to three halogen atoms,

A is —CO— or $SO_2$—

B is a $C_3$-$C_7$-cycloalkyl group; a $C_3$-$C_7$-cycloalkenyl group; or a 3- to 7-membered saturated or monounsaturated cyclic group with one hetero atom selected from the group consisting of: epoxyethyl, tetrahydrothienyl, tetrahydrothiopyranyl, xanthenyl, dihydrofuranyl, dihydrothienyl and dihydropropanyl, where the cycloalkyl groups or the cycloalkenyl group may be fused with one or two cycloalkyl groups of this type or with one or two benzene nuclei, where the total number of ring members is from 3 to 16 and these cyclic radicals may carry up to three of the following groups: halogen, $C_1$-$C_4$-alkyl, $C_2$-$C_6$-alkenyl, $C_1$-$C_6$-alkynyl and/or phenyl; a mononuclear to trinuclear aromatic or heteroaromatic radicals selected from phenyl; naphthyl; anthracenyl; phenanthrenyl; pyrrolyl; pyrazolyl; imidazolyl; triazolyl; pyridyl; pyrimidyl; pyrazinyl; pyridazinyl; quinolyl; isoquinolyl; furanyl; thienyl; isoxaolyl; oxaolyl; oxathiazolyl; isothiazolyl; thiozalyl; or thiodiozlyl; which radicals may carry up to three of the following groups $C_1$-$C_4$-alkyl, $C_1$-$C_4$-haloalkyl, $C_1$-$C_4$- alkoxy, C₁–C₄-haloalkoxy, C₁–C₄-alkylthio, C₁–C₄-slkylsulfinyl, C₁–C₄-alkylsulfonyl, cyano, nitro, carbo-C₁–C₄-alkoxy, N,N-di-C₁–C₄-alkylcarbamido and/or halogen.

2. A 5-amino-6-pyridazone compound of the formula Ib

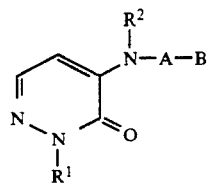

where
R¹ is C₁–C₄-alkyl which may carry up to three halogen atoms,
R² is C₁–C₄-alkyl or C₃–C₆-alkenyl, where these groups may carry up to two phenyl radicals, or C₃–C₆-alkynyl, A is —CO— or —SO₂—,
B is a C₃–C₇-cycloalkyl group; a C₃–C₇-cycloalkenyl group; or a 3- to 7-membered saturated or monounsaturated cyclic group with one hetero atom selected from the group consisting of: epoxyethyl, tetrahydrothienyl, tetrahydrothiopyranyl, xanthenyl, dihydrofuranyl, dihydrothienyl and dihydropropanyl, where the cycloalkyl groups or the cycloalkenyl group may be fused with one or two cycloalkyl groups of this type or with one or two benzene nuclei, where the total number of ring members is from 3 to 16 and these cyclic radicals may carry up to three of the following groups: halogen, C₁–C₄-alkyl, C₂–C₆-alkenyl, C₁–C₆-alkynyl and/or phenyl; a mononuclear to trinuclear aromatic or heteroaromatic radicals selected from phenyl; naphthyl; anthracenyl; phenanthrenyl; pyrrolyl; pyrazolyl; imidazolyl; triazolyl; pyridyl; pyrimidyl; pyrazinyl; pyridazinyl; quinolyl; isoquinolyl; furanyl; thienyl; isoxaolyl; oxaolyl; oxathiazolyl; isothiazolyl; thiozalyl; or thiodiozlyl; which radicals may carry up to three of the following groups C₁–C₄-alkyl, C₁–C₄-haloalkyl, C₁–C₄-alkoxy, C₁–C₄-haloalkoxy, C₁–C₄-alkylthio, C₁–C₄-slkylsulfinyl, C₁–C₄-alkylsulfonyl, cyano, nitro, carbo-C₁–C₄-alkoxy, N,N-di-C₁–C₄-alkylcarbamido and/or halogen.

3. A method for combating the growth of unwanted plants which method comprises contacting the unwanted plants with a herbicidally effective amount of at least one 5-amino-6-pyridazone compound of the formula Ia or Ib

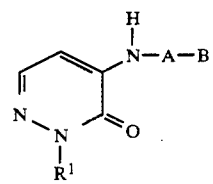

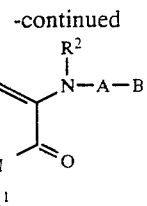

where
R¹ is C₁–C₄-alkyl which may carry up to three halogen atoms,
R² is C₁–C₄-alkyl or C₃–C₆-alkenyl, where these groups may carry up to two phenyl radicals, or C₃–C₆-alkynyl, A is —CO— or —SO₂—,
B is a C₃–C₇-cycloalkyl group; a C₃–C₇-cycloalkenyl group; or a 3- to 7-membered saturated or monounsaturated cyclic group with one hetero atom selected from the group consisting of: epoxyethyl, tetrahydrothienyl, tetrahydrothiopyranyl, xanthenyl, dihydrofuranyl, dihydrothienyl and dihydropropanyl, where the cycloalkyl groups or the cycloalkenyl group may be fused with one or two cycloalkyl groups of this type or with one or two benzene nuclei, where the total number of ring members is from 3 to 16 and these cyclic radicals may carry up to three of the following groups: halogen, C₁–C₄-alkyl, C₂–C₆-alkenyl, C₁–C₆-alkynyl and/or phenyl; a mononuclear to trinuclear aromatic or heteroaromatic radicals selected from phenyl; naphthyl; anthracenyl; phenanthrenyl; pyrrolyl; pyrazolyl; imidazolyl; triazolyl; pyridyl; pyrimidyl; pyrazinyl; pyridazinyl; quinolyl; isoquinolyl; furanyl; thienyl; isoxaolyl; oxaolyl; oxathiazolyl; isothiazolyl; thiozalyl; or thiodiozlyl; which radicals may carry up to three of the following groups C₁–C₄-alkyl, C₁–C₄-haloalkyl, C₁–C₄-alkoxy, C₁–C₄-haloalkoxy, C₁–C₄-alkylthio, C₁–C₄-slkylsulfinyl, C₁–C₄-alkylsulfonyl, cyano, nitro, carbo-C₁–C₄-alkoxy, N,N-di-C₁–C₄-alkylcarbamido and/or halogen.

4. A compound of the formula Ia as defined in claim 1, wherein A is CO, B is phenyl and R¹ is methyl.

5. A compound of the formula Ia as defined in claim 1, wherein A is SO₂, B is phenyl and R¹ is methyl.

6. A compound of the formula Ia as defined in claim 1, wherein A is CO, B is 2-chlorophenyl and R¹ is methyl.

7. A compound of the formula Ia as defined in claim 1, wherein A is CO, B is 4-chloro-3-thienyl and R¹ is CH₃.

8. A method for combatting the growth of unwanted plants, wherein the unwanted plants are treated with a herbicidally effective amount of the substituted pyridazone compound defined in claim 4.

9. A method for combatting the growth of unwanted plants, wherein the unwanted plants are treated with a herbicidally effective amount of the substituted pyridazone compound defined in claim 5.

10. A method for combatting the growth of unwanted plants, wherein the unwanted plants are treated with a herbicidally effective amount of the substituted pyridazone compound defined in claim 6.

11. A method for combatting the growth of unwanted plants, wherein the unwanted plants are treated with a herbicidally effective amount of the substituted pyridazone compound defined in claim 7.

* * * * *

UNITED STATES PATENT AND TRADEMARK OFFICE
CERTIFICATE OF CORRECTION

PATENT NO. : 5,123,952
DATED : June 23, 1992
INVENTOR(S) : Ulrich WRIEDE et al.

It is certified that error appears in the above-identified patent and that said Letters Patent is hereby corrected as shown below:

Claim 1, column 30, line 53: "groups" should read -- group --

Claim 1, column 30, line 59: "$C_1-C_6$-alky-" should read -- $C_2-C_6$-alky- --

Claim 1, column 31, line 2: "slkylsulfinyl" should read -- alkylsulfinyl --

Claim 2, column 31, line 51, "slkylsulfinyl" should read -- alkylsulfinyl --

Claim 3, column 32, line 39, "slkylsulfinyl" should read -- alkylsulfinyl --

Signed and Sealed this

Second Day of November, 1993

Attest:

BRUCE LEHMAN

Attesting Officer

Commissioner of Patents and Trademarks